United States Patent [19]
Horwell et al.

[11] Patent Number: 5,063,242
[45] Date of Patent: Nov. 5, 1991

[54] 7-((SUBSTITUTED)AMINO)-8-((SUB-STITUTED)CARBONYL)-METHYLAMINO)-1-OXASPIRO(4,5)DECNAES AS DIURETICS ANTIINFLAMMATORY, AND CEREBROVASCULAR AGENTS

[75] Inventors: David C. Horwell, Foxton; David C. Rees, Cambridge, both of England

[73] Assignee: Warner-Lambert Company, Morris Plains, N.J.

[21] Appl. No.: 551,583

[22] Filed: Jul. 11, 1990

Related U.S. Application Data

[62] Division of Ser. No. 341,336, Apr. 21, 1989, Pat. No. 4,965,278.

[51] Int. Cl.⁵ ............................................. A01N 43/38
[52] U.S. Cl. ...................................................... 514/414
[58] Field of Search ............................................. 514/414

[56] References Cited

U.S. PATENT DOCUMENTS 4,499,286  2/1985  Binder .................................. 548/527
4,598,087  7/1986  Horwell ............................... 514/429
4,663,343  5/1987  Horwell et al. ..................... 514/429
4,737,493  4/1988  Horwell ............................... 514/212

FOREIGN PATENT DOCUMENTS 0254545  1/1988  European Pat. Off. .
0258095  3/1988  European Pat. Off. .
0258096  3/1988  European Pat. Off. .
0260041  3/1988  European Pat. Off. .
0260555  3/1988  European Pat. Off. .
0261842  3/1988  European Pat. Off. .

Primary Examiner—Stanley J. Friedman
Assistant Examiner—T. J. Criares
Attorney, Agent, or Firm—Elizabeth M. Anderson

[57] ABSTRACT

Methods for using substituted phenoxy-, 1-, and 2-naphthalenyloxy-, indenyl-, indolyl-, benzo[b]-furanyl-, and benzo[b]thienylcarboxamides of 7,8-(substituted-diamino)-1-oxaspiro[4.5]decanes as cerebrovascular, diuretic, and antiinflammatory agents are disclosed. Pharmaceutical compositions employing the compounds are also disclosed.

3 Claims, 1 Drawing Sheet

7-((SUBSTITUTED)AMINO)-8-((SUBSTITUTED)-CARBONYL)-METHYLAMINO)-1-OXASPIRO(4,5-)DECNAES AS DIURETICS ANTIINFLAMMATORY, AND CEREBROVASCULAR AGENTS

This is a divisional of U.S. application Ser. No. 341,336 filed Apr. 21, 1989, now U.S. Pat. No. 4,965,278.

BACKGROUND OF THE INVENTION

The present invention is related to a method of using 7-((substituted)amino-8-((substituted)carbonyl)-methylamino)-1-oxaspiro(4.5)decanes and the pharmaceutically acceptable salts thereof as diuretic, antiinflammatory, and cerebrovascular agents. The compounds, processes for preparing them, and pharmaceutical compositions containing them are found in U.S. Pat. No. 4,737,493, which is herein incorporated by reference. The disclosed utility in the patent is analgesic. The compounds are also disclosed as having sedative, diuretic, and corticosteroid elevating effects and therefore as being useful diuretic and psychotherapeutic agents.

U.S. Pat. No. 4,598,087 covers certain substituted trans-1,2-diamino-cyclohexyl amide compounds which demonstrate selective opioid receptor binding. They are disclosed as useful as analgesics, diuretics, and psychotherapeutic agents.

U.S. Pat. No. 4,663,343 covers certain substituted naphthalenyloxy-1,2-diaminocyclohexyl amide compounds which possess selective kappa opioid receptor site binding activity and are useful as analgesics and diuretics.

European Application 258,095A discloses decahydroquinoline derivatives and European application 258,096 covers 1,2-diaminoindane derivatives. The compounds are analgesics with strong affinity for opiate receptors. The compounds are also mentioned as having diuretic, antiarrhythmic, cerebral antiischemic and hypotensive activity.

European Application 260,041 covers 1-acylsubstituted piperidine derivatives useful as analgesics with specific agonist effect on K receptors.

European Application 261,842 covers certain acylated-(1-(phenyl or benzyl)-1,2-ethylene diamines which are K-receptor agonists which act as analgesics through interaction with kappa opioid receptors.

European Application 254,545 covers 1,2-ethylene diamine compounds having analgesic, diuretic and antiinflammatory activity.

U.S. Pat. No. 4,499,286 covers transcyclohexane-1,2-diamine derivatives of thienylacetic acid. The compounds are disclosed as having analgesic activity.

European Application 260,555 covers benzo-fused cycloalkane and oxa- and thia-, cycloalkane trans-1,2-diamine derivatives useful as analgesic and diuretics.

SUMMARY

The present invention relates to a new method for treating cerebrovascular disorders. Such disorders include, but are not limited to, cerebral ischemia or cerebral infarction resulting from a range of conditions such as thromboembolic or hemorrhagic stroke. The method of treatment comprises administering to a patient in need of such treatment a therapeutically effective amount of a compound of formula I as described hereinafter.

Compounds of formula I are also useful as diuretics and antiinflammatory agents.

Pharmaceutical compositions are also included in the present invention.

DETAILED DESCRIPTION

Figure 1A:
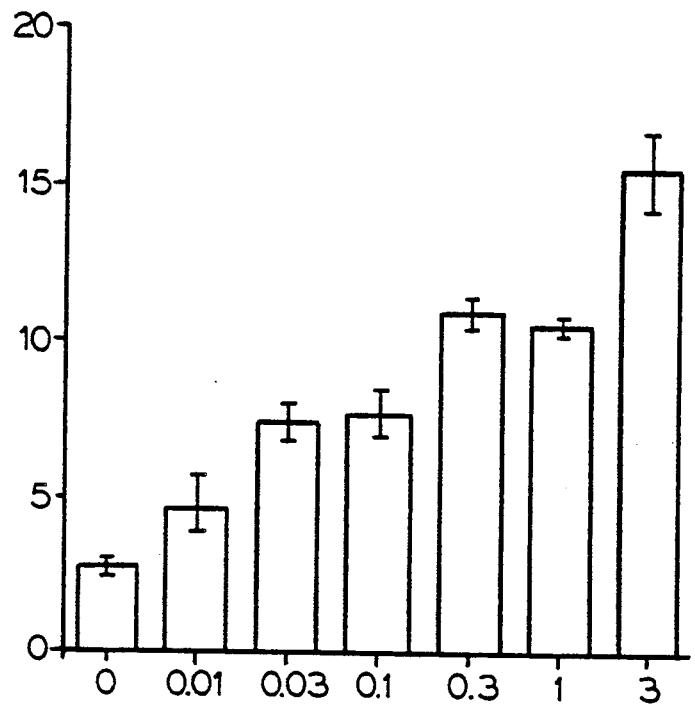
Figure 1B:
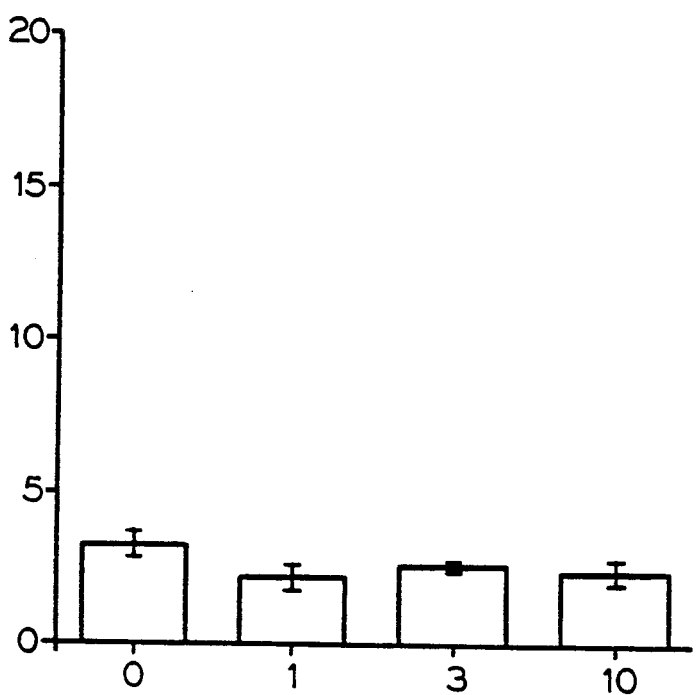

The present invention provides certain substituted oxaspirodiaminocyclohexane compoundswhich are useful as diuretic, antiinflammatory, and cerebrovascular agents. The compounds are

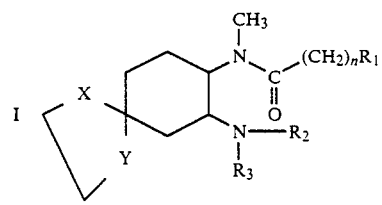

wherein n is an integer of from one to six; either of X or Y is oxygen and the other is —$CH_2$—; $R_1$ is selected from a) 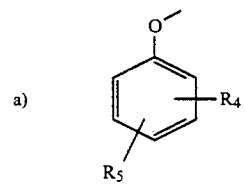

where $R_4$ and $R_5$ are independently hydrogen, fluorine, chlorine, bromine, nitro, trifluoromethyl, alkyl of from one to six carbon atoms, alkoxy of from one to six carbon atoms, or aryl;

3,4,5-trimethylphenoxy;

c) 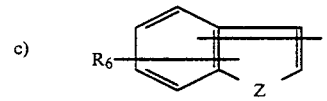

where $R_6$ is hydrogen, fluorine, chlorine, alkyl of from one to six carbon atoms, or aryl; Z is —$CH_2$—, —O—, —S—, or —$NR_7$— where $R_7$ is hydrogen, alkanoyl of from one to six carbon atoms, or alkyl of from one to six carbon atoms;

d) 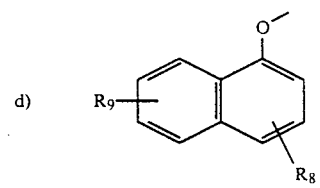

where $R_8$ and $R_9$ are independently hydrogen, fluorine, bromine, alkyl of from one to six carbon atoms, or alkoxy of from one to four carbon atoms; or e) 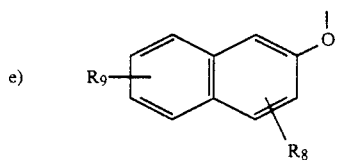

where R$_8$ and R$_9$ are as defined above; R$_2$ is methyl and R$_3$ is hydrogen, alkyl of from one to six carbon atoms,

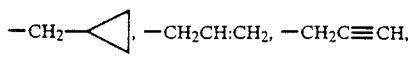

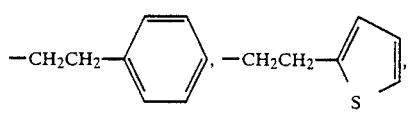

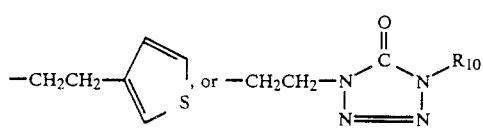

where R$_{10}$ is alkyl of from one to four carbon atoms; or where R$_2$ and R$_3$ when taken together with the nitrogen atom to which they are attached, form a pyrrolidinyl, piperidinyl, or hexahydro-1H-azepinyl ring; and the pharmaceutically acceptable acid addition salts thereof.

The compounds of the present invention constitute a class of derivatives of certain substituted oxaspirodiaminocyclohexane compounds of formula I above in which one nitrogen atom is an amine nitrogen substituted with methyl and a second substituent selected from the group R$_3$ as defined above, or when taken together with the nitrogen atom to which they are attached, R$_2$ and R$_3$ form a pyrrolidinyl, piperidinyl, or hexahydro-1H-azepinyl ring, and the other nitrogen atom is a N-methyl amide nitrogen further substituted with the group R$_1$ as defined above.

Compounds of the present invention contain one or more asymmetric carbon atoms and therefore exist in various stereoisomeric forms. Additionally, the compounds of this invention are capable of existing in different geometric isomeric forms. For example, the oxgen atom of the 5-membered spiro-ring may be positioned on the same side of the average plane of the cyclohexane ring as the amide nitrogen, or on the side opposite. The present invention contemplates all geometric and stereoisomeric forms of the compounds of formula I above.

The individual stereosiomers are obtained, if desired, from mixture of the different forms by known methods of resolution such as the formation of diastereomers, followed by recrystallization.

Compounds of the instant invention include solvates, hydrates, and salts of formula I above.

Preferred compounds of the present invention are those of formula I above wherein R$_1$ is

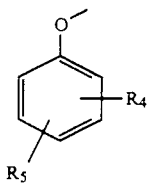

where R$_4$ and R$_5$ are independently hydrogen, fluorine, chlorine, bromine, nitro, trifluoromethyl, alkyl of from one to six carbon atoms, alkoxy of from one to six carbon atoms, or aryl.

By the term "aryl" is meant phenyl; phenyl substituted with fluorine, chlorine, alkoxy of from one to four carbon atoms, nitro, or trifluoromethyl; 2- or 3-thienyl; and 2- or 3-thienyl substituted with alkyl of from one to four carbon atoms or alkoxy of from one to four carbon atoms.

Preferred compounds of the present invention are those of formula I above where R! is

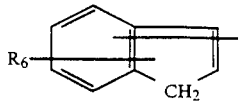

wherein R$_6$ is as defined above. The most preferred compounds are substituted inden-1-yl compounds of formula I above.

Other preferred compounds of the present invention are those of formula I wherein R is

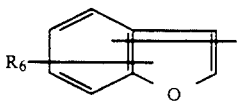

wherein R$_6$ is as defined above. The most preferred compounds are substituted benzofuran-4-yl compounds of formula I.

Yet other preferred compounds of the present invention are those of-formula I wherein R$_1$ is

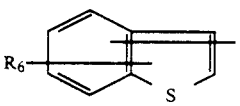

wherein R$_6$ is as defined above. The most preferred compounds are substituted benzo[b]thiophen-4-yl compounds of formula I.

Yet other preferred compounds of the present invention are those of formula I wherein R$_1$ is

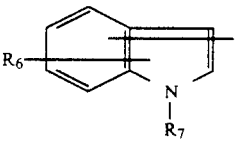

wherein R$_6$ and R$_7$ are as defined above. The most preferred compounds are indol-4-yl compounds of formula I.

Yet other preferred compounds of the present invention are those of formula I wherein $R_1$ is

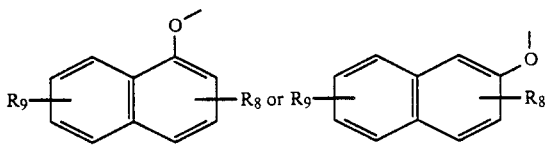

wherein $R_8$ and $R_9$ are independently hydrogen, flourine, chlorine, bromine, alkyl of from one to four carbon atoms or alkoxy of from one to four carbon atoms.

Preferred substituents for $R_2$ and $R_3$ are those where $R_2$ is methyl and $R_3$ is lower alkyl, most preferably methyl, or where $R_2$ and $R_3$ taken together with the nitrogen atom to which they are attached form a pyrrolidinyl ring.

Preferred compounds of the present invention include but are not limited it:

[5R-(5α,7α,8β)]-N-Methyl-N-[7-(methyl-2-propynylamino)-1-oxaspiro[4.5]dec-8-yl]-2-phenoxyacetamide,

[5S-(5α,7α,8β)]-N-Methyl-N-[7-(methyl-2-propynylamino)-1-oxaspiro[4.5]dec-8-yl]-2-phenoxyacetamide,

[5R-(5α,7α,8β)]-N-Methyl N-[7-(methyl-2-propynylamino)-1-oxaspiro[4.5]dec-8-yl]-2-phenoxyacetamide,

[5S-(5α,7α,8β)]-N-Methyl-N-[7-(methyl-2-propynylamino)-1-oxaspiro[4.5]dec-8-yl]-2-phenoxyacetamide,

[5R-(5α,7α,8β)]-2-(4-Fluorophenoxy)-N-methyl-N-[7-(1-pyrrolidinyl)]-1-oxaspiro[4.5]dec-8-yl]acetamide,

[5S-(5α,7α,8β)]-2-(4-Fluorophenoxy)-N-methyl-N-[7-(1-pyrrolidinyl)]-1-oxaspiro[4.5]dec-8-yl]acetamide,

[5R-(5α,7α,8β)]-2-(4-Fluorophenoxy)-N-methyl-N-[7-(1-pyrrolidinyl)]-1-oxaspiro[4.5]dec-8-yl]acetamide,

[5S-(5α,7α,8β)]-2-(4-Fluorophenoxy)-N-methyl-N-[7-(1-pyrrolidinyl)]-1-oxaspiro[4.5]dec-8-yl]acetamide,

[5R-(5α,7α,8β)]-2-(4-Fluorophenoxy)-N-methyl-N-[7-[methyl-(2-phenylethyl)amino]-1-oxaspiro[4.5]dec-5R-(5α,7α,8β)]-2-(4-Fluorophenoxy)-N-methyl-N-8-yl]acetamide,

[5S-(5α,7α,8β)]-2-(4-Fluorophenoxy)-N-methyl-N-[7-[methyl-(2-phenylethyl)amino]-1-oxaspiro[4.5]dec-8-yl]acetamide,

[5R-(5α,7α,8β)]-2-(4-Fluorophenoxy)-N-methyl-N-[7-[methyl-(2-phenylethyl)amino]-1-oxaspiro[4.5]dec-8-yl]acetamide,

[5S-(5α,7α,8β)]-2-(4-Fluorophenoxy)-N-methyl-N-[7-[methyl-(2-phenylethyl)amino]-1-oxaspiro[4.5]dec-8-yl]acetamide,

[5R-(5α,7α,8β)]-N-Methyl-2-(3-nitrophenoxy)-N-[7-(1-pyrrolidinyl)-1-oxaspiro[4.5]dec-8-yl]acetamide,

[5S-(5α,7α,8β)]-N-Methyl-2-(3-nitrophenoxy)-N-[7-(1-pyrrolidinyl)-1-oxaspiro[4.5]dec-8-yl]acetamide,

[5R-(5α,7α,8β)]-N-Methyl-2-(3-nitrophenoxy)-N-[7-(1-pyrrolidinyl)-1-oxaspiro[4.5]dec-8-yl]acetamide,

[5S-(5α,7α,8β)]-N-Methyl-2-(3-nitrophenoxy)-N-[7-(1-pyrrolidinyl)-1-oxaspiro[4.5]dec-8-yl]acetamide,

[5R-(5α,7α,8β)]-N-Methyl-N-[7-(1-pyrrolidinyl)-1-oxaspiro[4.5]dec-8-yl]-2-[3-(trifluoromethyl)phenoxy]acetamide,

[5S-(5α,7α,8β)]-N-Methyl-N-[7-(1-pyrrolidinyl)-1-oxaspiro[4.5]dec-8-yl]-2-[3-(trifluoromethyl)phenoxy]acetamide,

[5R-(5α,7α,8β)]-N-Methyl-N-[7-(1-pyrrolidinyl)-1-oxaspiro[4.5]dec-8-yl]-2-[3-(trifluoromethyl)phenoxy]acetamide,

[5S-(5α,7α,8β)]-N-Methyl-N-[7-(1-pyrrolidinyl)-1-oxaspiro[4.5]dec-8-yl]-2-[3-(trifluoromethyl)phenoxy]acetamide,

[5R-(5α,7α,8β)]-2-(3,4-Dichlorophenoxy)-N-methyl-N-[7-(1-pyrrolidinyl)-1-oxaspiro[4.5]dec-8-yl]acetamide,

[5S-(5α,7α,8β)]-2-(3,4-Dichlorophenoxy)-N-methyl-N-[7-(1-pyrrolidinyl)-1-oxaspiro[4.5]dec-8-yl]acetamide,

[5R-(5α,7α,8β)]-2-(3,4-Dichlorophenoxy)-N-methyl-N-[7-(1-pyrrolidinyl)-1-oxaspiro[4.5]dec-8-yl]acetamide,

[5S-(5α,7α,8β)]-2-(3,4-Dichlorophenoxy)-N-methyl-N-[7-(1-pyrrolidinyl)-1-oxaspiro[4.5]dec-8-yl]acetamide,

[5R-(5α,7α,8β)]-2-(2,6-Dichlorophenoxy)-N-methyl-N-[7-(1-pyrrolidinyl)-1-oxaspiro[4.5]dec-8-yl]acetamide,

[5S-(5α,7α,8β)]-2-(2,6-Dichlorophenoxy)-N-methyl-N-[7-(1-pyrrolidinyl)-1-oxaspiro[4.5]dec-8-yl]acetamide,

[5R-(5α,7α,8β)]-2-(2,6-Dichlorophenoxy)-N-methyl-N-[7-(1-pyrrolidinyl)-1-oxaspiro[4.5]dec-8-yl]acetamide,

[5S-(5α,7α,8β)]-2-(2,6-Dichlorophenoxy)-N-methyl-N-[7-(1-pyrrolidinyl)-1-oxaspiro[4.5]dec-8-yl]acetamide,

[5R-(5α,7α,8β)]-2-(3,5-Dichlorophenoxy)-N-methyl-N-[7-(1-pyrrolidinyl)-1-oxaspiro[4.5]dec-8-yl]acetamide,

[5S-(5α,7α,8β)]-2-(3,5-Dichlorophenoxy)-N-methyl-N-[7-(1-pyrrolidinyl)-1-oxaspiro[4.5]dec-8-yl]acetamide,

[5R-(5α,7α,8β)]-2-(3,5-Dichlorophenoxy)-N-methyl-N-[7-(1-pyrrolidinyl)-1-oxaspiro[4.5]dec-8-yl]acetamide,

[5S-(5α,7α,8β)]-2-(3,5-Dichlorophenoxy)-N-methyl-N-[7-(1-pyrrolidinyl)-1-oxaspiro[4.5]dec-8-yl]acetamide,

[5R-(5α,7α,8β)]-N-Methyl-2-(1-naphthalenyloxy)-N-[7-(1-pyrrolidinyl)-1-oxaspiro[4.5]dec-8-yl]acetamide,

[5S-(5α,7α,8β)]-N-Methyl-2-(1-naphthalenyloxy)-N-[7-(1-pyrrolidinyl)-1-oxaspiro[4.5]dec-8-yl]acetamide,

[5R-(5α,7α,8β)]-N-Methyl-2-(1-naphthalenyloxy)-N-[7-(1-pyrrolidinyl)-1-oxaspiro[4.5]dec-8-yl]acetamide,

[5S-(5α,7α,8β)]-N-Methyl-2-(1-naphthalenyloxy)-N-[7-(1-pyrrolidinyl)-1-oxaspiro[4.5]dec-8-yl]acetamide,

[5R-(5α,7α,8β)]-N-Methyl-2-(2-naphthalenyloxy)-N-[7-(1-pyrrolidinyl)-1-oxaspiro[4.5]dec-8-yl]acetamide,

[5S-(5α,7α,8β)]-N-Methyl-2-(2-naphthalenyloxy)-N-[7-(1-pyrrolidinyl)-1-oxaspiro[4.5]dec-8-yl]acetamide,

[5R-(5α,7α,8β)]-N-Methyl-2-(2-naphthalenyloxy)-N-[7-(1-pyrrolidinyl)-1-oxaspiro[4.5]dec-8-yl]acetamide,

[5S-(5α,7α,8β)]-N-Methyl-2-(2-naphthalenyloxy)-N-[7-(1-pyrrolidinyl)-1-oxaspiro[4.5]dec-8-yl]acetamide,

[5R-(5α,7α,8β)]-N-Methyl-N-[7-[methyl[2-(2thienyl)ethyl]-amino]-1-oxaspiro[4.5]dec-8-yl]-2-naphthalenyloxy)acetamide,

[5S-(5α,7α,8β)]-N-Methyl-N-[7-[methyl[2-(2-thienyl)ethyl]amino]-1-oxaspiro[4.5]dec-8-yl]-2-(1naphthalenyloxy)acetamide,

[5R-(5α,7α,8β)]-N-Methyl-N-[7-[methyl[2-(2thienyl)ethyl]amino]-1-oxaspiro[4.5]dec-8-yl]-2-(1naphthalenyloxy)acetamide, 5S-(5α,7α,8β)]-N-Methyl-N-[7-[methyl[2-(2thienyl)ethyl]amino]-1-oxaspiro[4.5]dec-8-yl]-2-(1naphthalenyloxy)acetamide, 5R-(5α,7α,8β)]-N-Methyl-N-[7-(methyl-2-propenylamino)-1-oxaspiro[4.5]dec-8-yl]-1H-indene-3-acetamide,

[5S-(5α,7α,8β)]-N-Methyl-N-[7-(methyl-2-propenylamino)-1-oxaspiro[4.5]dec-8-yl]-1H-indene-3-acetamide,

[5R-(5α,7α,8β)]-N-Methyl-N-[7-(methyl-2-propenylamino)-1-oxaspiro[4.5]dec-8-yl]-1H-indene-3-acetamide,

[5S-(5α,7α,8β)]-N-Methyl-N-[7-(methyl-2-propenylamino)-1-oxaspiro[4.5]dec-8-yl]-1H-indene-3-acetamide,

[5R-(5α,7α,8β)]-N-Methyl-[7-(1-pyrrolidinyl)-1-oxaspiro[4.5]dec-8-yl]-1H-indene 3-acetamide,

[5S-oxaspiro[5α,7α,8β)]-N-Methyl-[7-(1-pyrrolidinyl)-1-4.5]dec-8-yl]-1H-indene-3-acetamide,

[5R-(5α,7α,8β)]-N-Methyl-[7-(1-pyrrolidinyl)-1oxaspiro[-4.5]dec-8-yl]-1H-indene-3-acetamide,

[5S-(5α,7α,8β)]-N-Methyl-[7-(1-pyrrolidinyl)-1oxaspiro[-4.5]dec-8-yl]-1H-indene-3-acetamide,

[5R-(5α,7α,8β)]-N-[7-(Dimethylamino)-1-oxaspiro[4.5]dec-8-yl]-N-methyl-1H-indole-3-acetamide,

[5S-(5α,7α,8β)]-N-[7-(Dimethylamino)-1-oxaspiro[-4.5]dec-8-yl]-N-methyl-1H-indole-3-acetamide,

[5R-(5α,7α,8β)]-N-[7-(Dimethylamino)-1-oxaspiro[-4.5]dec-8-yl]-N-methyl-1H-indole-3-acetamide,

[5S-(5α,7α,8β)]-N-[7-(Dimethylamino)-1-oxaspiro[-4.5]dec-8-yl]-N-methyl-1H-indole-3-acetamide,

[5R-(5α,7α,8β)]-N-Methyl-N-[7-(1-pyrrolidinyl)-1oxaspiro[-4.5]dec-8-yl]-1H-indole-3-acetamide,

[5S-(5α,7α,8β)]-N-Methyl-N-[7-(1-pyrrolidinyl)-1oxaspiro[-4.5]dec-8-yl]-1H-indole-3-acetamide,

[5R-(5α,7α,8β)]-N-Methyl-N-[7-(1-pyrrolidinyl)-1oxaspiro[-4.5]dec-8-yl]-1H-indole-3-acetamide,

[5S-(5α,7α,8β)]-N-Methyl-N-[7-(1-pyrrolidinyl)-1oxaspiro[-4.5]dec-8-yl]-1H-indole-3-acetamide,

[5R-(5α,7α,8β)]-N-Methyl-N-[7-(1-pyrrolidinyl)-1oxaspiro[-4.5]dec-8-yl]-2-benzofuranacetamide,

[5S-(5α,7α,8β)]-N-Methyl-N-[7-(1-pyrrolidinyl)-1oxaspiro[-4.5]dec-8-yl]-2-benzofuranacetamide,

[5R-(5α,7α,8β)]-N-Methyl-N-[7-(1-pyrrolidinyl)-1oxaspiro[-4.5]dec-8-yl]-2-benzofuranacetamide,

[5S-(5α,7α,8β)]-N-Methyl-N-[7-(1-pyrrolidinyl)-1oxaspiro[-4.5]dec-8-yl]-2-benzofuranacetamide,

[5R-(5α,7α,8β)]-N-Methyl-N-[7-(1-pyrrolidinyl)-1oxaspiro[-4.5]dec-8-yl]-3-benzofuranacetamide,

[5S-(5α,7α,8β)]-N-Methyl-N-[7-(1-pyrrolidinyl)-1oxaspiro[-4.5]dec-8-yl]-3-benzofuranacetamide,

[5R-(5α,7α,8β)]-N-Methyl-N-[7-(1-pyrrolidinyl)-oxaspiro[-4.5]dec-8-yl]-3-benzofuranacetamide,

[5S-(5α,7α,8β)]-N-Methyl-N-[7-(1-pyrrolidinyl)-1-oxaspiro[4.5]dec-8-yl ]-3-benzofuranacetamide,

[5R-(5α,7α,8β)]-N-Methyl-N-[7-(1-pyrrolidinyl)-1oxaspiro[-4.5]dec-8-yl]-4-benzofuranacetamide, 5S-(5α,7α,8β)]-N-Methyl-N-[7-(1-pyrrolidinyl)-1-[oxaspiro[4.5]dec-8-yl]-4-benzofuranacetamide,

[5S-(5α,7α,8β)]-N-Methyl-N-[7-(1-pyrrolidinyl)-1oxaspiro[-4.5]dec-8-yl]-4-benzofuranacetamide,

[5R-(5α,7α,8β)]-N-[7-[(Cyclopropylmethyl)methylamino]-1-oxaspiro[4.5]dec-8-yl]-N,2-dimethyl-3-benzofuranacetamide,

[5S-(5α,7α,8β)]-N-[7-[(Cyclopropylmethyl)methylamino]-1-oxaspiro[4.5]dec-8-yl]-N,2-dimethyl-3-benzofuranacetamide,

[5R-(5α,7α,8β)]-N-[7-[(Cyclopropylmethyl)methylamino]-1-oxaspiro44.5]dec-8-yl]-N,2-dimethyl-3-benzofuranacetamide,

[5S-(5α,7α,8β)]-N-[7-[(Cyclopropylmethyl)methylamino]-N-1-oxaspiro[4.5]dec-8-yl]-N,2-dimethyl-3-benzofuranacetamide.

More preferred compounds of the present invention include but are not limited to:

(−)(5α,7α,8β)-N-methyl-N-[7-pyrrolidinyl)-1-oxaspiro[4.5]dec-8-yl]-4-benzo[b]furacetamide, and (−)(5α,7α,8β)-N-7-(1-pyrrolidinyl)-1-oxaspiro[4.5]dec-8-yl]-4-benzo[b]thiophene-4-acetamide The compounds of formula I of the present invention have a very high kappa opioid affinity, selectivity and potency. For example, (−)-(5α,7α,8β)-N-methyl-N-[7-(1-pyrrolidinyl)-1-oxaspiro[4.5]dec-8yl]-4-benzo[b-]furanacetamide gives a Ki of 0.73 nM with a μ/kappa ratio of 798. The MPEso in the rat paw pressure test for analgesia is 0.030 (iv) This is considerably better than any selective kappa opioid compound known to the inventors.

The compounds of the present invention possess significant analgesic activity, as disclosed in U.S. Pat. No. 4,737,493, with the potential for minimum dependence liability due to their selective kappa opioid receptor properties. In addition to acting as analgesics, selective kappa opioid agonists also cause opioid receptor-mediated sedation, diuresis, and corticosteroid elevations. Accordingly, the compounds of the present invention are also useful diuretics, antiinflammatories, and psychotherapeutic agents.

The compounds of the formula I of the present invention also have application in congestive heart failure, advanced hepatic cirrhosis, nephrotic syndrome, chronic renal failure, trauma associated with surgery, emotional and physical stress, endocrine disorders, syndrome of inappropriate antidiuretic hormone secretion, and therapy with certain pharmacologic drug agents such as certain sulfonyl ureas, clofibrate, certain tricyclics such as carbamazipine, amitriptyline, thiothixene, flubenzaine, and thioridazine, certain antineoplastic agents, certain analgesics, and certain natriuretic diuretics.

The compounds of formula I of the present invention also have neuroprotective indications. As such, they are useful in the treatment of stroke and the treatment of cerebral ischemia (P. F. Vonvoightlander in *Brain Research* 435:174–180 (1987) and A. H. Tang, et al in *Brain Research* 403:52–57 (1987).)

The effectiveness of the aforementioned compounds as neuroprotective agents is determined by a pharmacological test procedure as described and illustrated below.

The surgical procedure is a modification of that originally proposed by A. Tamura, et al, *J. Cerb. Blood Flow Metab.*, 1:53–60 (1981). It is similar to the methods described by D. Duverger, et al, *J. Cereb. Blood Flow Metab.* 8:449–461 (1988), and by S. Brint, et al, *J. Cereb. Blood Flow Metab.* 8:474–485 (1988). Male F-344 rats weighing 300–350 g were anesthetized in 2% halothane in room air. The right femoral vein was cannulated and the tubing led subcutaneously to an exit behind the neck to allow intravenous (IV) drug injection. The left common carotid was permanently occluded with a 6-0 silk ligature. The left middle cerebral artery (MCA) was exposed through a 2-mm burr hole drilled 1-2 mm rostral to the fusion of the zygomatic arch with the squamosal bone. The dura was cut, the MCA lifted off the surface of the brain, electrocauterized, and cut. The wound margins were sutured shut and the anesthesia stopped.

The compound,(−)-(5α,7α,8β)-N-methyl-N-[7-1-pyrrolidinyl)-1-oxaspiro[4.5]dec-8-yl]-4benzo[b-]furanacetamide, (0.5 mg/kg) and vehicle (0.9% saline) were administered IV 30 minutes and 24 hours after occlusion to groups of 12 animals each. Forty-eight hours following occlusion rats were anesthetized with ketamine (150 mg/kg, IP), decapitated, the brains rapidly removed, and placed on ice. With the aid of a brain mold (Activational Systems), the brain was sliced into four 2-mm sections: one section anterior to the MCA and three sections posterior to the MCA. The sections were then placed for 30 minutes in a 2% solution of 2,3,5-triphenyltetrazolium chloride (TTC) in saline. The brains were stored in 10% neutral buffered saline for analysis.

The brains were coded and the analysis was performed blind. The area of infarction in each section was outlined with the aid of a morphometric analysis program (Bioquant IV, R & M Biometrics). The TTC stain is converted into a red marker in live mitochondria, while the infarcted area remains white. The total volume of infarction was calculated from the areas of the four sections assuming two truncated cones. The mean area for each section and the mean total volume were calculated; vehicle and drug treatment were compared using the Student's t-test. The means±standard deviation, % change, and statistical data are presented in Table I.

TABLE I

| Section | Infarct Size (mm$^2$)* Saline | Compound** (0.5 mg/kg) | Decrease | t-value | Probability |
|---|---|---|---|---|---|
| Anterior | 8.9 ±5.4 | 6.5 ±1.9 | −26.4 | 1.42 | 0.168 |
| Anterior Medial | 12.3 ±4.9 | 7.8 ±2.8 | −36.8 | 2.76 | 0.011 |
| Posterior Medial | 10.8 ±8.5 | 4.0 ±5.2 | −62.7 | 2.35 | 0.028 |
| Posterior | 9.3 ±8.7 | 1.8 ±4.1 | −80.9 | 2.7 | 0.012 |
| Total Volume | 63.1 ±38.5 | 30.1 ±18.4 | −52.3 | 2.68 | 0.013 |

*mm$^3$ for total volume
**Compound is (−)-(5α,7α,8β)-N-methyl-N-[7-1-pyrrolidinyl)-1-oxaspiro[4.5]dec-8-yl]-4-benzo[b]furanacetamide In summary, the compound produced a significant decrease in the infarct area in three of the four brain sections and in the total volume. The data support the beneficial activity in the treatment of focal brain ischemia.

The compound, (−)-(5α,7α,8β)-N-methyl-N-[7-1-pyrrolidinyl)-1-oxaspiro[4.5]dec-8-yl]-4-benzo[b-]furanacetamide, was tested in carrageenan footpad edema test. Rats were injected IV with the compound, dissolved in saline, and administered at a final vehicle volume of 0.15 ml/kg. Fifteen minutes later the rats were injected in one rear footpad with 0.05 ml of a 1% solution of carrageenan. Five hours later swelling was measured in the injected hindpaw by mercury plethysmography. Indomethacin, a standard cyclooxygenase inhibitor, was administered orally as a control. The results are summarized in Table II below.

TABLE II

| Compound* | Route | Dose (mg/kg) | N | Delta Edema (x ± SEM) | % I | P Value |
|---|---|---|---|---|---|---|
| Vehicle | IV | | 10 | 77 ± 4.7 | | |
| Test compound | IV | 0.01 | 10 | 55 ± 4.9 | 29 | >0.01 |
| | IV | 0.03 | 10 | 50 ± 3.2 | 36 | >0.001 |
| | IV | 0.1 | 10 | 49 ± 2.5 | 37 | >0.001 |
| | IV | 0.3 | 9 | 29 ± 3.9 | 63 | >0.001 |
| | IV | 1.0 | 9 | 19 ± 3.7 | 75 | >0.001 |
| Indomethacin | PO | 5.0 | 10 | 40 ± 2.5 | 48 | >0.001 |

*As can be seen in the above table, the test compound is a potent inhibitor of the acute inflammatory response in rats The diuretic effect of compounds of the instant invention is demonstrated below in Table III.

It is well established that kappa opiate agonists produce water diuresis in rats as in D. C. Horwell, *Drugs of the Future*, 13 1068 (1988). One highly selective kappa agonist is (±)-(5α,7α,8β)-N-methyl-N[7-(1-pyrrolidinyl)-1-oxaspiro[4.5]dec-8-yl]-4benzo[b]furanacetamide, which is a mixture of two enantiomers. In vitro receptor binding studies demonstrate that the (−) enantiomer of the compound possesses very high affinity and selectivity for the kappa receptor and that the (+) enantiomer has much lower affinity.

Following subcutaneous administration a compound of the instant invention (−)-(5α,7α,8β)-N-methyl-N[7-1-pyrrolidinyl)-1-oxaspiro[4.5]dec-8-yl]-4-benzo[b-]furanacetamide, (−) enantiomer, produced a dose-related increase in the volume of urine produced over the six-hour test period (Table III). The maximum volume of urine produced by the highest dose tested was comparable to the maximum effect produced by (±)-(5α,7α,8β)-N-methyl-N-[7-(1-pyrrolidinyl)-1oxaspiro[-4.5]dec-8-yl]-4-benzo[b]furanacetamide: 15.5±1.2 ml for the (−)isomer(−), (−)-(5α,7α,8β)-N-methyl-N-[7-1-pyrrolidinyl)-1-oxaspiro[4.5]dec-8-yl]-4-benzofuranacetamide compared to 14.9 ±0.7 ml for the racemate(±), (±)-(5α,7α,8β)-N-methyl-N-[7-(1-pyrrolidinyl)-1-oxaspiro[4.5]dec-8-yl]-4-benzo[b]-furanacetamide. As was expected from the in vitro receptor binding assays which suggested that the (+) enantiomer has negligible affinity for the kappa receptor, this compound was found to have no effect on urine output, as is shown in Figure IIIb.

These results together confirm that the kappa opiate receptor activity of the compound (±)-(5α,7α,8β)-N-methyl-N-[7-(1-pyrrolidinyl)-1oxaspiro[4.5]dec-8-yl]-4-benzo[b]furanacetamide resides entirely in the (−) enantiomer with the (+) enantiomer having no activity in the rat diuresis test, a reliable and sensitive test for detecting kappa opiate agonist activity in vivo.

A comparison of the effects of (a) (−) enantiomer and (b) (+) enantiomer on urine output in the normally hydrated rat. Both compounds were dissolved in saline and administered subcutaneously in a dose volume of 1 ml/kg. Vehicle-treated controls received saline only. The data shown represent mean values (±SEM) for groups of six animals per dose level.

For the therapeutic uses described above, the usual mammalian dosage range for a 70-kg human subject is from 0.01 to 10 mg per day or 0.001 mg to 1.0 mg per kg of weight per day; optionally in divided portions. Determination of the proper dosage for a particular situation is within the skill of the art.

Pharmaceutical compositions of the compound of the present invention or its salts are produced by formulating the active compound in dosage unit form with a pharmaceutical carrier. Some examples of dosage unit forms are tablets, capsules, pills, powders, aqueous and nonaqueous oral solutions, and suspensions and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerin; sorbitol; polyethylene glycol; water; agar; alginic acid; isotonic saline; and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits, but for practical purposes it is preferably present in a concentration of at least 10% in a solid composition and at least 2% in a primarily liquid composition. The most satisfactory compositions are those in which a much higher proportion of the active ingredient is present.

Routes of administration of the subject compound or its salts are oral, parenteral, transdermal, or intranasal. For example, a useful intravenous dose is between 0.001 and 10 mg/kg. A preferred intravenous dose is 0.01 to 1 mg/kg. A still further preferred dose is 0.01 to 0.55 mg/kg. A useful oral dose is 0.01 to 30 mg/kg.

The following examples of formulations are provided to enable one skilled in the art to practice the invention. These examples are not intended to limit the scope of the invention in any way but rather to be illustrative thereof. Compound I is a compound of formula I as described hereinbefore.

EXAMPLE 1

Injectables

Compound I, Water for injection USP q.s.

The hydrochloride salt of Compound I is dissolved in water and passed through a 0.2-micron filter. Aliquots of the filtered solution are added to ampoules or vials, sealed, and sterilized.

EXAMPLE 2

Syrups 2 mg Compound I/5 ml syrup

| | |
|---|---|
| Compound I | 12.5 g |
| Purified Water USP | 200 ml |
| Cherry Syrup qu | 1000 ml |

Compound I is dissolved in the water and to this solution the syrup is added with mild stirring.

EXAMPLE 3

Capsules o.5 mg, 1 mg, or 2 mg

| | |
|---|---|
| Compound I | 250 g |
| Lactose USP, Anhydrous q.s. or | 250 g |
| Sterotex Powder HM | 5 g |

Combine Compound I and the lactose in a tumble, blend for two minutes, blend for one minute with the intensifier bar, and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds, and tumble-blended for an additional minute. The appropriately sized capsules are filled with 141 mg, 352.5 mg, or 705 mg of the blend, respectively, for the 50-mg, 125-mg, and 250-mg containing capsules.

EXAMPLE 4

Tablets 0.5 mg, 1 mg, or 2 mg

| | |
|---|---|
| Compound I | 125 g |
| Corn Starch NF | 200 g |
| Cellulose, Microcrystalline | 46 g |
| Sterotex Powder HM | 4 g |
| Purified Water q.s. or | 300 ml |

Combine the corn starch, the cellulose, and Compound I together in a planetary mixer and mix for two minutes. Add the water to this combination and mix for one minute. The resulting mix is spread on trays and dried in a hot air oven at 50° C. until a moisture level of 1 to 2 percent is obtained. The dried mix is then milled with a Fitzmill through a #RH2B screen, and added back to the milled mixture and the total blended for five minutes by drum rolling. Compressed tablets of 0.150 mg, 3.75 mg, and 7.50 mg, respectively, of the total mix are formed with appropriate sized punches the 0.50 mg, 1.25 mg, or 5.00 mg containing tablets.

We claim:

1. A method for treating inflammation which comprises administering to a patient in need of said treatment a therapeutically effective amount of a compound in unit dosage form of formula

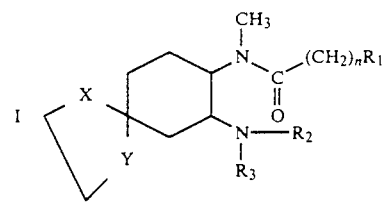

or a pharmaceutically acceptable salt thereof, wherein n is an integer of from one to six; either of X or Y is oxygen and the other is —CH$_2$—; R is selected from a) 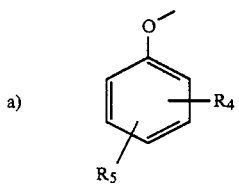

where R$_4$ and R$_5$ are independently hydrogen, fluorine, chlorine, bromine, nitro, trifluoromethyl, alkyl of from one to six carbon atoms, alkoxy of from one to six carbon atoms, or aryl;

b) 3,4,5-trimethylphenoxy;

c) 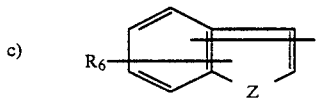

where R$_6$ is hydrogen, fluorine, chlorine, alkyl of from one to six carbon atoms, or aryl; Z is —CH$_2$—, —O—, —S—, or —NR$_7$— where R$_7$ is hydrogen, alkanoyl of from one to six carbon atoms, or alkyl of from one to six carbon atoms;

d) 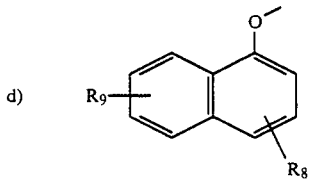

wherein R$_8$ and R$_9$ are independently hydrogen, fluorine, bromine, alkyl of from one to six carbon atoms, or alkoxy of from one to four carbon atoms; or e) 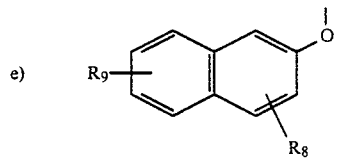

where R$_8$ and R$_9$ are as defined above; where R$_2$ is methyl and R$_3$ is hydrogen, alkyl of from one to six carbon atoms,

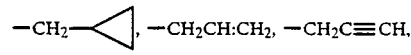

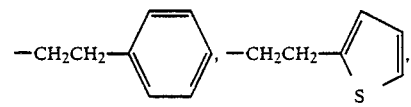

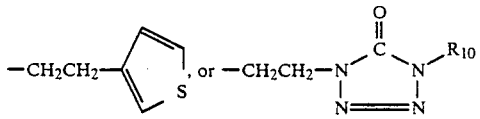

where R$_{10}$ is alkyl of from one to four carbon atoms; or where R$_2$ and R$_3$ when taken together with the nitrogen atom to which they are attached, form a pyrrolidinyl, piperidinyl, or hexahydro-1H-azepinyl ring.

2. A method according to claim 1 wherein the compound is (−)-(5α,7α,8β)-N-methyl-N-[7-(1-pyrrolidinyl)-1-oxaspiro[4.5]dec-8-yl]-4benzo[b]furanacetamide.

3. A method according to claim 1 wherein 0.001 mg to 1 mg/kg of weight per day of the compound or the pharmaceutically acceptable salt is administered.

* * * * *